(12) United States Patent
Graw

(10) Patent No.: US 7,774,879 B2
(45) Date of Patent: Aug. 17, 2010

(54) PILLOW FOR A PATIENT DURING A MEDICAL PROCEDURE

(75) Inventor: Ansgar Graw, Chicago, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 338 days.

(21) Appl. No.: 11/439,791

(22) Filed: May 23, 2006

(65) Prior Publication Data

US 2007/0271702 A1  Nov. 29, 2007

(51) Int. Cl.
*A47G 9/10* (2006.01)
(52) U.S. Cl. ............................................. 5/636; 5/646
(58) Field of Classification Search ................ 5/623, 5/632, 636, 646, 647
See application file for complete search history.

(56) References Cited

U.S. PATENT DOCUMENTS

| | | | | |
|---|---|---|---|---|
| RE24,377 E | * | 10/1957 | Creelman | .................. 5/603 |
| 3,038,175 A | * | 6/1962 | Faget et al. | ............... 244/171.9 |
| 4,728,566 A | * | 3/1988 | Lancaster et al. | ............ 442/226 |
| 4,979,519 A | | 12/1990 | Chavarria et al. | |
| 5,203,041 A | * | 4/1993 | Alonso | .......................... 5/420 |
| 5,742,963 A | * | 4/1998 | Trevino et al. | .................. 5/632 |
| 6,049,927 A | * | 4/2000 | Thomas et al. | .................. 5/632 |
| 6,459,927 B1 | | 10/2002 | Franklin et al. | |
| 6,622,727 B2 | * | 9/2003 | Perry | .......................... 128/845 |

* cited by examiner

*Primary Examiner*—Robert G Santos
*Assistant Examiner*—Gilbert Y Lee
(74) *Attorney, Agent, or Firm*—Peter L. Kendall

(57) ABSTRACT

An accessory for a patient's use during a medical procedure is disclosed. The accessory includes a pillow that has an inner material and an outer material. The pillow includes a head support, at least one shoulder support and at least one hand support. The head support has a right side, a left side and a top side. The shoulder support is disposed adjacent the right side and/or the left side of the head support. The hand support is disposed adjacent the top side of the head support. The inner material of the pillow is made of a substantially rigid material. The outer material of the pillow is made of a substantially soft material.

9 Claims, 4 Drawing Sheets

PILLOW FOR A PATIENT DURING A MEDICAL PROCEDURE

BACKGROUND

The present invention relates to a pillow for a patient during a medical procedure, and more particularly relates to a type of pillow used to support a patient's head, shoulders, arms and hands during medical imaging procedures to increase the patient's comfort.

Medical imaging procedures such as, for example, SPECT (Single Photon Emission Computed Tomography) and SPECT-CT (CAT Scan), often require a patient to lie down on a surface and to remain as motionless as possible. To obtain SPECT images, a gamma camera is generally rotated around the patient and projections are acquired at defined points during the rotation, typically about every 3-6 degrees. A 360 degree rotation is commonly used to obtain an optimal reading. It generally takes about 15-20 seconds to take each projection, thus the approximate time of a total reading is at least 15-20 minutes. Therefore, a patient must remain as still as possible while lying down for over 15 minutes. As can be appreciated, this can be quite difficult and uncomfortable for the patient. Further, additional testing may be required if the patient does not remain still enough. To ameliorate this procedure for the patient, a head pillow may be provided for the patient to rest his head on.

Other issues result when a patient's torso is being imaged. In such situations, it is often required for the patient to remove one or both of his arms from the imaging area. To comply with this requirement, the patient usually places his arms over his head (and on the surface that he is lying on). Here, even when a pillow is provided for the patient to rest his head on, the patient's shoulders, arms and hands do not have a comfortable surface to rest on. To remedy this problem, patients may be given additional pillows to rest these body parts on. In addition to introducing more non-essential elements into the imaging machine, the inclusion of additional pillows often does not provide the patient with a desired level of comfort.

The present invention includes a pillow that enables a patient to rest his head, shoulders, arms and hands on during a medical procedure, such as an imaging procedure.

SUMMARY

The present invention relates to an accessory (pillow) for a patient's use during a medical procedure (e.g., an imaging procedure, such as SPECT (Single Photon Emission Computed Tomography) and SPECT-CT (CAT Scan)). The pillow includes a head support, at least one shoulder support (e.g. two shoulder supports), at least one hand support (e.g., two hand supports) and at least one ergonomic transition. The head support has a right side, a left side and a top side. The shoulder support is disposed adjacent the right side and/or the left side of the head support. The hand support is disposed adjacent the top side of the head support. The ergonomic transition is disposed between the head support and at least one shoulder support, between the head support and at least one hand support and/or between at least one shoulder support and at least one hand support. An embodiment of the present disclosure also includes the accessory having at least one arm support (e.g., two arm supports) between a shoulder support and a hand support.

In a disclosed embodiment, the pillow is made of an inner material and an outer material. The inner material of the pillow may be made of a substantially rigid and comfortable material (e.g., Polyethylene foam, Polystyrene foam, or other low-attenuating plastic materials and any reasonable combinations thereof) and the outer material may be made of a substantially soft (or foam) material (e.g., Polyolefins such as Polyethylene, Polypropylene or other low-attenuating materials and any reasonable combinations thereof).

In another embodiment of the present invention, a skin (which may be removable) is included which substantially encases the pillow. In this embodiment, a pad is also included which is insertable between the skin and the outer material. A pad is also included which may be positioned on the outer material. Such pads provide additional comfort to the patient.

The present invention also relates to an accessory (pillow) for a patient's use during a medical procedure that includes a head support having a rigidly defined right side, left side and top side. The pillow also includes two shoulder supports, two hand supports and two arm supports.

BRIEF DESCRIPTION OF THE DRAWINGS

Exemplary embodiments of the present invention are described hereinbelow with reference to the figures wherein.

DETAILED DESCRIPTION OF EXEMPLARY EMBODIMENTS

Embodiments of the presently disclosed accessory for a patient's use during a medical procedure are described in detail with reference to the drawings wherein like numerals designate identical or corresponding elements in each of the several views.

Figure 1:
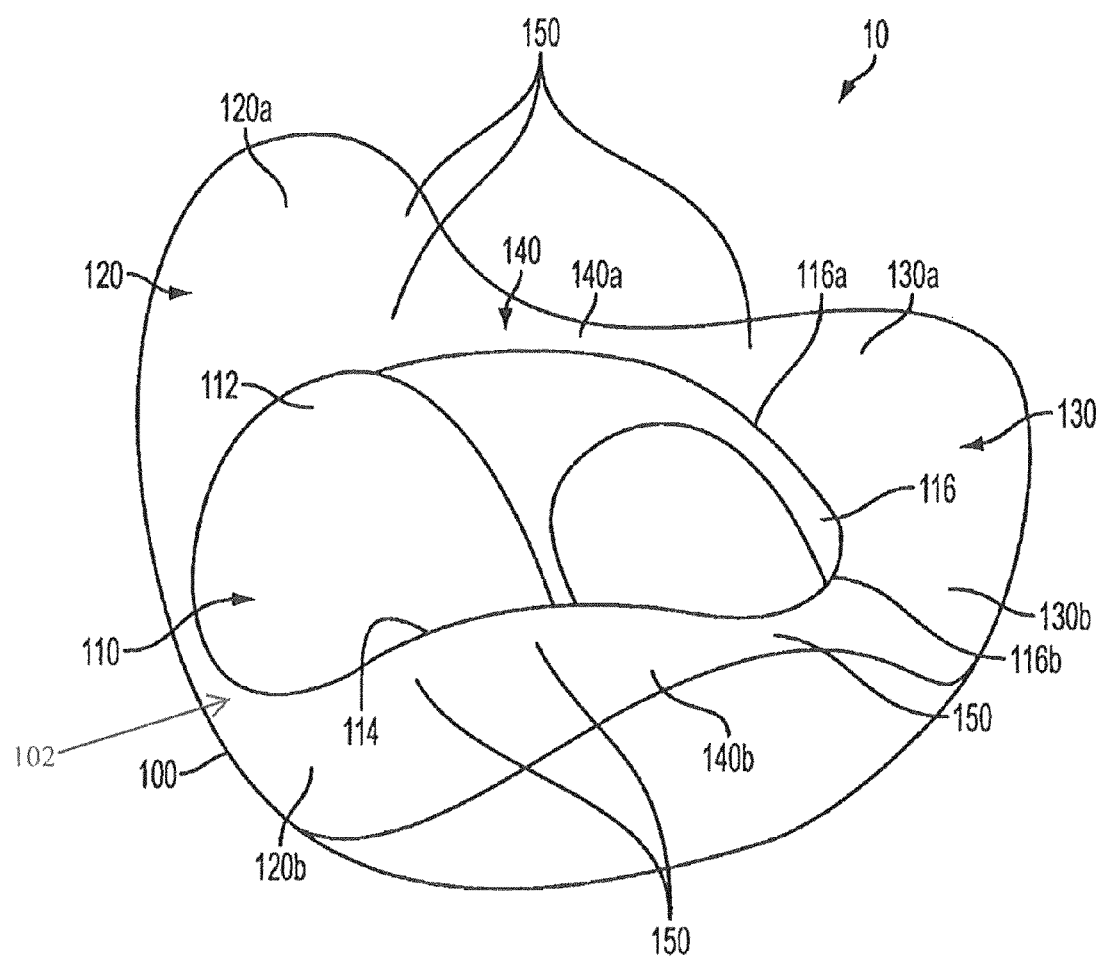
FIG. 1 is a perspective view of an accessory for a patient's use during a medical procedure.
Figure 2:
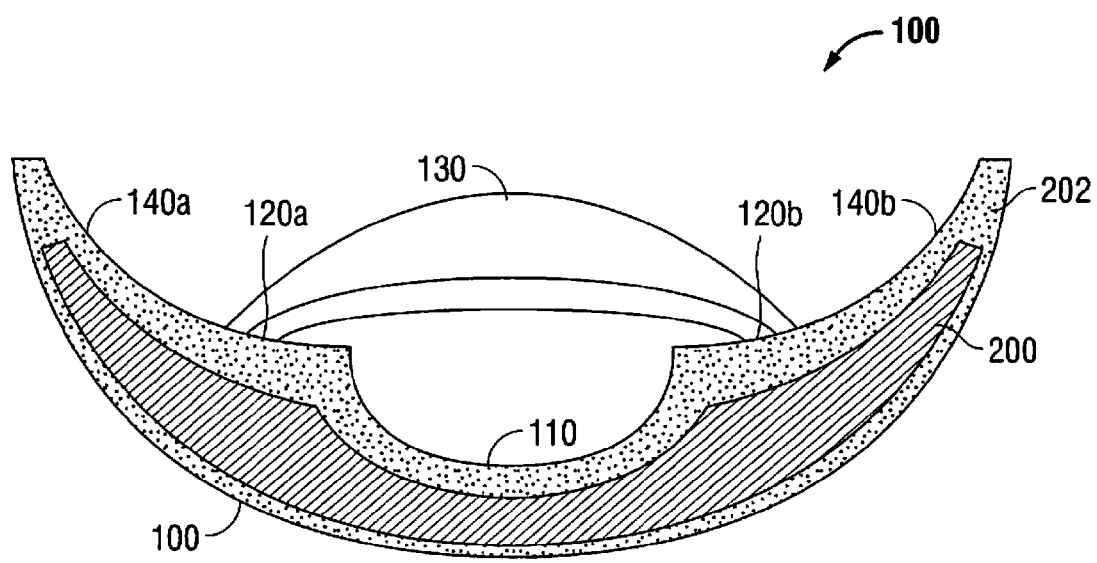
FIG. 2 is a front, cross-sectional view of the accessory of FIG. 1.

Referring to FIGS. 1-4, an accessory for a patient's use during a medical procedure (e.g., SPECT (Single Photon Emission Computed Tomography) and SPECT-CT (CAT Scan)) is shown and is generally referred to by reference numeral 10. Accessory 10 is designed to support at least the head, a shoulder and a hand of a patient "P" (FIG. 3) during a medical procedure, such as an imaging procedure, where it is desirable for the patient to be lying down. Accessory 10 includes a pillow 100 being made of an inner material 200 and an outer material 202, outer material 202 being disposed at least partially around inner material 200 (FIG. 2).

With specific reference to FIG. 1, pillow 100 of this embodiment is illustrated having a base edge surface 102, a head support 110, a pair of shoulder supports 120, a pair of hand supports 130 and a pair of arm supports 140. As can be appreciated, head support 110 is dimensioned to support the head of a patient, shoulder supports 120 are dimensioned to support the shoulders of a patient, hands supports 130 are dimensioned to support the hands of a patient and arm supports 140 are dimensioned to support the arms of a patient.

With continued reference to FIG. 1, head support 110 includes a right side 112, a left side 114 and a top side 116. Top side 116 of head support 110 includes a right portion 116a and a left portion 116b. Shoulder supports 120 include a right shoulder support 120a that is designed to support a patient's right shoulder and a left shoulder support 120b that is designed to support a patient's left shoulder. Right shoulder support 120a is disposed adjacent right side 112 of head support 110 and left shoulder support 120b is disposed adjacent left side 114 of head support 110. Hand supports 130 include a right hand support 130a for supporting a patient's right hand and a left hand support 130b for supporting the left hand of a patient. Right hand support 130a is disposed adjacent right portion 116a of top side 116 of head support 110. Left hand support 130b is disposed adjacent left portion 116b of top side 116 of head support 110. Arm supports 140 include a right arm support 140a for supporting a patient's right arm and a left arm support 140b, which is designed to support the left arm of a patient. Right arm support 140a is disposed between right shoulder support 120a and right hand support 130a. Left arm support 140b is disposed between left shoulder support 120b and left hand support 130b.

With continued reference to FIG. 1, a plurality of ergonomic transitions 150 is also illustrated on pillow 100. Ergonomic transitions 150 are the areas of pillow 100 that are between various supports and may increase a patient's overall comfort. For example, ergonomic transitions 150 are illustrated between head support 110 and shoulder supports 120, between shoulder supports 120 and arms supports 140 and between arm supports 140 and hand supports 130. As can be appreciated, ergonomic transitions 150 may be disposed between any combination of head support 110, shoulder supports 120, hand supports 130 and arm supports 140. Further, ergonomic transitions 150 are envisioned to be included between any of the supports and the periphery of pillow 100 and even within a single support for accepting contours of a body part.

Figure 4:
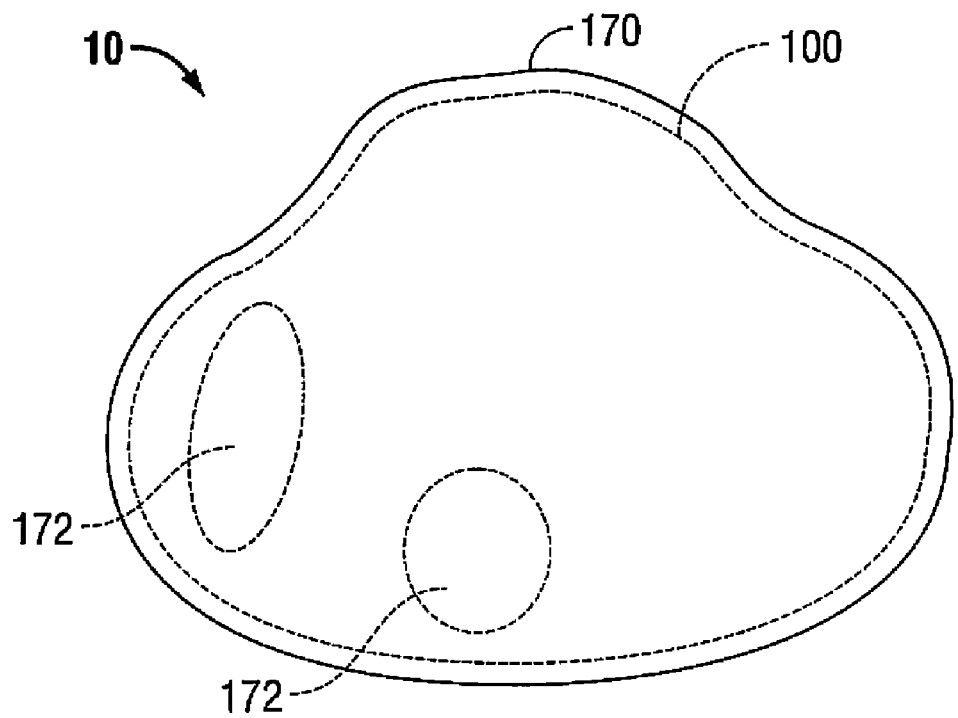
FIG. 4 is a top view of the accessory of FIGS. 1-3 and including a skin.

With particular reference to FIG. 2, pillow 100 is made of an inner material 200 and an outer material 202. Inner material 200 may be made of a substantially rigid and/or flexible material, such as low-attenuating plastic materials including Polyethylene, Polystyrene foam or any other suitable material or reasonable combinations thereof. Outer material 202, which comes into contact with a patient (when skin 170, as discussed below with reference to FIG. 4, is not in place), may be made of a substantially soft (foam) material, such as Polyolefins including Polyethylene, Polypropylene, other low-attenuating materials, or any other suitable material or reasonable combinations thereof. As illustrated in FIG. 2, outer material 202 substantially encapsulates inner material 200, thus resulting in pillow 100 being soft to the touch and durable.

The cross-sectional shape of pillow 100 is also illustrated in FIG. 2. As illustrated in this embodiment, arm supports 140 and hand support 130 are curved upward. Cross-sections of pillow 100 having other shapes are also envisioned and within the scope of the present invention.

Figure 3:
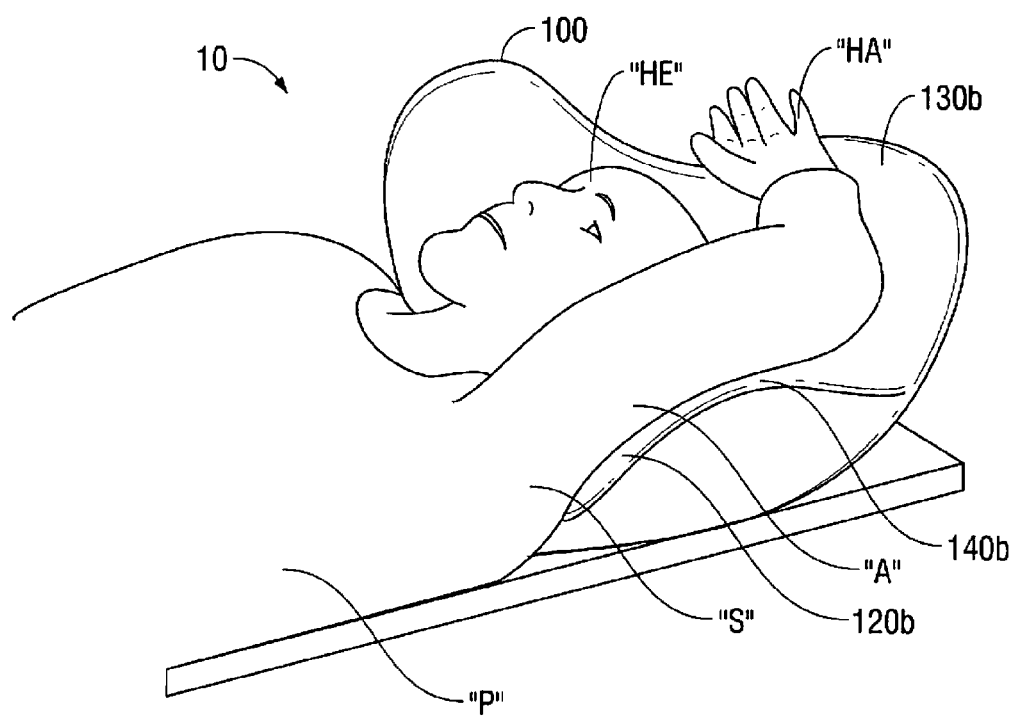
FIG. 3 is a perspective, in situ view of the accessory of FIGS. 1 and 2.

With reference to FIG. 3, a patient "P" is illustrated using pillow 110. As shown, the patient's head "HE" is resting on head support 100. The patient's left shoulder "S" is resting on left shoulder support 120b. The patient's left arm "A" is being supported by left arm support 140b. And the patient's left hand "HA" is resting on left hand support 130b. For clarity, the patient's right shoulder, arm and hand are not explicitly shown in FIG. 3.

Now referring to FIG. 4, skin 170 is illustrated substantially encasing pillow 100. In an embodiment, skin 170 is configured to follow the contours of pillow 100, resulting in a snug fit. It is envisioned that skin 170 is removable from pillow 100 to enable changing and/or washing of skin 170. Skin 170 may be made from a synthetic material such as a Polyolefin, including Polyethylene. Polypropylene or other low-attenuating material. In an envisioned embodiment, skin 170 is made of a cleanable and puncture resistant synthetic material, such as "leatherette." Skin 170 may be made of the same material or of a different material as outer material 202. An example of when skin 170 and outer material 202 may be made of the same material is when the application of a thermoforming process creates skin 170 when outer material 202 is heated.

A pad or plurality of pads 172 may be inserted between outer material 202 of pillow 100 and skin 170 to provide additional softness and/or support in particular areas. It is contemplated that pads 172 may be configured as various regular or irregular shapes and may be directly applied to outer material 202 of pillow 100 (e.g., via an adhesive surface on pad 172) without using skin 170.

It is further contemplated by the present invention that a variety of pillows 100 may be sized to accommodate the various body parts of different-sized people, such as children and adults. It is also envisioned that pillow 100 is used to only support a patient's head during a procedure that does not require the patient to place his arms above his head.

While several embodiments of the invention have been shown in the figures, it is not intended that the invention be limited thereto, as it is intended that the invention be as broad in scope as the art will allow and that the specification be read likewise. Therefore, the above description should not be construed as limiting, but merely as exemplifications of various embodiments. Those skilled in the art will envision other modifications within the scope and spirit the claims appended hereto.

What is claimed is:

1. An accessory for a patient's use during a medical procedure, comprising:
   a pillow having a base edge surface;
   left and right upwardly directed shoulder supports formed on opposite ends of the base edge surface, adapted for abutment of respective left and right shoulders of a patient, each shoulder support forming an elevated peak portion;
   an upwardly directed hand support distal the base edge surface, forming an elevated peak portion;
   a concave head support formed in the base edge surface, extending from the base edge surface toward the hand support, adapted for cradling a patient's head;
   left and right arm supports formed between the head support and respective left and right shoulder supports; and
   left and right hand supports formed between the head support and the hand support elevated peak portion contiguous with the respective left and right arm supports;
   wherein the left and right shoulder support peaks and hand support peak define a generally triangular plan form, the respective shoulder supports defining left and right base vertices and the hand support defining an apex vertex.

2. The accessory according to claim 1, wherein the pillow includes a substantially rigid inner material and a substantially soft outer material, the outer material being made from a material selected from the group consisting of Polyethylene and Polypropylene.

3. The accessory according to claim 1, wherein the pillow includes a substantially rigid inner material and a substantially soft outer material, the inner material being made from a material selected from the group consisting of Polyethylene and Polystyrene.

4. The accessory according to claim 1, further comprising a skin substantially encasing the pillow.

5. The accessory according to claim 4, wherein the skin is removable from the pillow.

6. The accessory according to claim 4, further comprising at least one pad which is insertable between the skin and an outer material for providing additional comfort to the patient.

7. The accessory according to claim 1, further comprising at least one pad which is positionable on an outer material for providing additional comfort to the patient.

8. The accessory according to claim 1, wherein the pillow is used during an imaging procedure.

9. The accessory according to claim 1, wherein the pillow is used during at least one of a SPECT (Single Photon Emission Computed Tomography) and a SPECT-CT (Computerized Tomography Scan) procedure.

* * * * *